US005667793A

United States Patent [19]

Cho et al.

[11] Patent Number: 5,667,793
[45] Date of Patent: Sep. 16, 1997

[54] SKIN CARE COMPOSITIONS FOR TREATING CELLULITE

[75] Inventors: Suk Hyung. Cho, Monroeville, Pa.; Norman Kramer Richardson, Rockaway Township, N.J.; Allan Robert Burger, Passaic, N.J.; Anita Marie Brinker, Midland Park, N.J.; Mark Edward Rerek, Scotch Plains, N.J.

[73] Assignee: Chesebrough-Pond's USA Co., Division of Conopco, Inc., Greenwich, Conn.

[21] Appl. No.: 691,992

[22] Filed: Aug. 2, 1996

[51] Int. Cl.⁶ ..................................... A61K 7/48
[52] U.S. Cl. ............... 424/401; 424/195.1; 514/937; 514/944
[58] Field of Search ............... 424/401, 195.1; 514/937, 944, 860

[56] References Cited

U.S. PATENT DOCUMENTS

| | | | |
|---|---|---|---|
| 4,501,734 | 2/1985 | Tanaka et al. | 514/198 |
| 4,525,359 | 6/1985 | Greenway et al. | 514/653 |
| 4,588,724 | 5/1986 | Greenway et al. | 514/250 |
| 5,194,259 | 3/1993 | Soudant et al. | 424/401 |
| 5,215,759 | 6/1993 | Mausner | 424/489 |

OTHER PUBLICATIONS

Cosmetics and toiletries magazine, vol. 111, pp. 61–70 Jul. 1995.
C& T ingredient resource series, pp. 21–27 Apr. 1994.
Derwent Abstract of EP 568001 dated Dec. 13, 1993.
Derwent Abstract of JP 04243832 dated Nov. 15, 1993.
Derwent Abstract of JP 63060918 dated Sep. 23, 1993.
Derwent Abstract of JP 2264727 dated Sep. 28, 1993.
CAPLUS Abstract of JP 52079032 dated Jun. 26, 1996.
CAPLUS Abstract of JP 50088238 dated Jun. 26, 1996.

*Primary Examiner*—Jyothsan Venkat
*Attorney, Agent, or Firm*—Rimma Mitelman

[57] ABSTRACT

Anti-cellulite compositions based on a lipolytic active, which is an extract of *Polygala tenuifolia*, an extract of *Platycodon grandiflorum*, or an extract of *Kochia scoparia*. When *Polygala tenuifolia* or *Platycodon grandiflorum* is employed, a polar solvent extract is preferred. The extracts are preferably employed in conjunction with a xanthine, e.g. caffeine or theophylline (which are preferably obtained from a natural source), in order to lower the cost of the compositions.

2 Claims, No Drawings

SKIN CARE COMPOSITIONS FOR TREATING CELLULITE

FIELD OF THE INVENTION

The present invention relates to the use of *Polygala tenuifolia*, *Platycodon grandiflorum* or *Kochia scoparia*, alone or in combination with a xanthine, for topical application.

BACKGROUND OF THE INVENTION

Cellulite is a term applied to a skin condition associated with the lumps, bumps and dimples that appear on the thighs of many women. This condition is frequently described as "orange peel skin", "mattress phenomena" or the "cottage cheese effect". Although the etiology of cellulite is poorly understood, the main etiological factor appears to be local accumulation of fat in a regional compartment. It has been proposed that the anatomical structure of subcutaneous adipose tissue is the major cause of cellulite. The histological studies of subcutaneous tissues from men and women suggest that the fat lobules are larger and more vertical in women than men. As a result, these larger, less restricted lobules can express outward against the dermis causing the bumps and dimples characteristic of cellulite. The femoral subcutaneous fat deposits in women also tend to be more lipogenic and less lipolytic than abdominal subcutaneous or visceral fat due to the difference in the distribution of alpha and beta adrenergic receptors on adipocytes in these different regions.

Topical application for the treatment of cellulite of agents capable of distributing or reducing local fat accumulation by lipolytic action thereby improving the aesthetic appearance of the skin has been used. Among the common agents for treatment of cellulite as slimming agents are xanthine analogs such as caffeine or theophylline. These agents block the antilipolytic action of adenosine, a potent endogenous inhibitor of lipolysis.

Other known methods in lipolysis stimulation are achieved by inhibiting phosphodiesterase in order to prevent or at least limit the degradation of cAMP. Xanthine based adenosine antagonists such as caffeine or theophylline are also known to be effective phosphodiesterase inhibitors.

Other existing methods for the treatment of cellulite have been the stimulation of adenylate cyclase to increase cAMP levels (beta adrenergic agonists) or to block the antilipolytic inactivation of adenylate cyclase (alpha-2-adrenergic antagonists). Greenway et al. (U.S. Pat. No. 4,588,724) disclose that isoproterenol, a known beta agonist (beta adrenergic stimulator), is effective for the treatment of cellulite by stimulating lipolysis. Greenway et al. (U.S. Pat. Nos. 4,588,724 and 4,525,359) disclose that creams based on yohimbine, a known alpha-2-blocker applied to women's skin showed a decrease in thigh circumference. Soudant et al. (U.S. Pat. No. 5,194,259) disclose a *Ginkgo biloba*, a known alpha-2-blocker, as a lipolytic agent in combination with at least one other alpha-2-blocker in a slimming cosmetic composition.

It has now been discovered in a quite unexpected manner that certain botanicals have the same or better lipolytic activity than the anti-cellulite agents described above. The present invention thus relates to the use of *Polygala tenuifolia*, *Platycodon grandiflorum* or *Kochia scoparia*, alone or in combination with other slimming agents, in anti-cellulite skin care compositions.

*Polygala tenuifolia* is a traditional Chinese herb which has been used for the treatment of coughs with little or no side effects. EP 568001 discloses oral administration of *Polygala tenuifolia* root and other Chinese, Japanese and Indonesian folk medicines for antiviral activity against herpes, polio, measles, Varicella, cytomegalovirus and/or DNA/RNA viruses. JP 04243832 discloses *Polygala tenuifolia* and other botanical extracts to be effective for the prevention and the treatment of systematic lupus erythematosus and rheumatoid arthritis. JP 02048514 discloses the use of Polygala root and other botanical extracts in promoting hair growth and hair loss prevention. JP 63060918 discloses antimicrobial oral composition containing *Polygala tenuifolia*. JP 2264727 discloses cosmetic compositions containing *Polygala tenuifolia*, but does not appear to mention cellulite.

*Platycodon grandiflorum* is traditionally used to dispel phlegm, relieve sore throats and to promote pus discharge. Tanaka et al. (U.S. Pat. No. 4,501,734) disclose the use of saponin from *Platycodon grandiflorum* in enhancing the oral or rectal delivery of antibiotics. Abstracts of JP 52079032 and JP 50088238 disclose cosmetic compositions containing *Platycodon grandiflorum*, but do not appear to mention cellulite.

The art described above does not teach the use of any presently claimed plant extracts as anti-cellulite agents and does not teach any topical compositions containing *Kochia scoparia*.

SUMMARY OF THE INVENTION

The present invention includes, in part, a skin care composition for reducing signs of cellulite, the composition comprising from about 0.0001% to about 5% of a plant extract selected from the group consisting of *Polygala tenuifolia*, *Platycodon grandiflorum*, *Kochia scoparia*, and mixtures thereof; and a cosmetically acceptable vehicle.

The invention also includes a method for reducing the signs of cellulite which includes application of the inventive compositions onto the skin.

DETAILED DESCRIPTION OF THE INVENTION

The inventive compositions require from about 0.0001% to about 5%, by weight of the composition of a plant extract selected from the group consisting of extracts of *Polygala tenuifolia*, *Platycodon grandiflorum*, and *Kochia scoparia*. Preferably, in order to maximize the lipolytic effect from 0.01% to 2% is employed, most preferably from 0.01% to 0.1%.

The whole plant may be employed, but preferably fruit of Kochia and the roots of Polygala and Platycodon.

These extracts may be prepared with solvents like ethanol, methanol, isopropanol, ethylene glycol, propylene glycol or water and any combination of these solvents to perform extraction or percolation. Other organic solvents like THF, ether, mineral oil or vegetable oil can also be used.

It has been discovered, as part of the present invention, that the lipolytic activity of *Polygala tenuifolia* is substantially higher in polar solvent extracts compared to nonpolar solvent extracts (see Example 3).

The extracts may be prepared with solvents as listed above. The plants may be obtained commercially from Wilhelm Krämer, Schwebheim, (Germany) or Campo Research (Singapore).

Compositions of the present invention will also contain a cosmetically acceptable carrier for the plant extract. Amounts of the carrier may range from about 60% to about 99.9%, preferably from about 80 to 99.5% by weight of the total composition. Included among the cosmetically acceptable carriers are emollients, surfactants, humectants, powders and water.

In the preferred embodiment of the invention, a cosmetically acceptable vehicle is comprised either of water or of a water/solvent blend. The solvent is optimally chosen from propylene glycol, ethanol, butylene glycol, and polyethylene glycols of various molecular weights.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the emulsion, and can, in the absence of other cosmetic adjuncts, form the balance of the composition.

Optional Skin Benefit Materials and Cosmetic Adjuncts

In a preferred method according to the present invention a xanthine is applied along with a plant extract to the cellulite-affected skin. The term "xanthine" as used herein includes the following compounds:

xanthine ($C_5H_4O_2N_4$);

1,3-dimethyl xanthine (commonly known as "theophylline");

3,7-dimethyl xanthine (commonly known as "theobromine");

trimethyl xanthine (commonly known as "caffeine");

alloxantin;

paraxanthine;

heteroxanthine;

salts of the above mentioned compounds (e.g., ethylenediamine salts of theophylline);

and mixtures thereof.

The preferred xanthine employed in the inventive method is caffeine and/or theophylline due to their availability and optimum efficacy. Caffeine and theophylline can be, and preferrably are naturally-derived, in order to keep with a "natural" character of the inventive compositions.

The xanthine is employed in the inventive method preferably in an amount of at least 0.05%, generally in the amount of from 0.05% to 20%, preferably in the amount of from 0.10% to 10%, optimally in the amount of from 0.5% to 3.0% by weight of the composition in order to maximize efficacy at optimum cost.

Another preferred ingredient employed in the inventive method is an alpha hydroxy acid. The presence of the alpha hydroxy acid facilitates the increase in the strength and firmness of dental and epidermal layers of the skin. Even more preferably, the hydroxy acid is chosen from lactic acid, glycolic acid, mandelic acid, and mixtures thereof to optimize the efficacy of compositions by increasing percutaneous absorption. In the most preferred embodiment of the invention, in order to maximize the performance of hydroxy acid, inventive compositions contain the L-form of an alpha hydroxy acid. Preferably the amount of the alpha hydroxy acid component present in the composition according to the invention is from 1.5% to 20%, more preferably from 1.5% to 15%, and most preferably from 3.0% to 12.0% by weight of the composition.

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be employed in the method of the present invention. Actives are defined as skin benefit agents other than emollients and other than ingredients that merely improve the physical characteristics of the composition. Although not limited to this category, general examples include sunscreens, tanning agents, skin anti-wrinkling agents, anti-inflammatory agents, skin lighteners and moisturizers.

Sunscreens include those materials commonly employed to block ultraviolet light. Illustrative compounds are the derivatives of PABA, and cinnamate. For example, octyl methoxycinnamate and 2-hydroxy-4-methoxybenzophenone (also known as oxybenzone) can be used. Octyl methoxy-cinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Suitable anti-inflammatory compounds include but are not limited to rosmarinic acid, glycyrrizinate derivatives, alpha bisabolol, azulene and derivatives thereof, asiaticoside, sericoside, ruscogenin, escin, esculin, quercetin, rutin, betulinic acid and derivatives thereof, catechin and derivatives thereof.

Suitable vasoactive compounds include but are not limited to papaverine, yohimbine, visnadin, khellin, bebellin, nicotinate derivatives.

Surfactants, which are also sometimes designated as emulsifiers, may be incorporated into the cosmetic compositions of the present invention. Surfactants can comprise anywhere from about 0.5% to about 30%, preferably from about 1% to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, taffy acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and/or dialkyl phosphates and sodium fatty acyl isethionate.

Amphoteric surfactants include such materials as dialkylamine oxide and various types of betaines (such as cocoamido propyl betaine).

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols; polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate(a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust bean gum. Under certain circumstances the thickening function may be accomplished by a material also serving as a silicone or emollient. For instance, silicone gums in excess of 10 centistokes and esters such as glycerol stearate have dual functionality. Cellulosic derivatives may also be employed, e.g., hydroxypropyl cellulose (Klucel HI®).

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic composition employed in the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

The method of the present invention is useful for reducing or preventing the appearance of cellulite, for improving the firmness and elasticity of skin and generally to enhance the quality and flexibility of skin.

The following examples will more fully illustrate the embodiments of this invention, but the invention is not limited thereto. All parts, percentages and proportions referred to herein and in the appended claims are by weight unless otherwise indicated.

Extraction of Botanicals

For Example 1 and 2, the extracts of the root bark of *Polygala tenuifolia*, the root of *Platycodon grandiflorum* or the fruit of *Kochia scoparia* were obtained from Shanghai Institute of Materia Medica (extracted in methanol, then concentrated to dryness).

The extracts used in Examples 3 and 4 were prepared by Soxhlet extraction with methanol of root bark of *Polygala tenuifolia*, roots of *Platycodon grandiflorum*, and fruits of *Kochia scoparia*. The extracts were concentrated to dryness under vacuum. Assay date indicated that these extracts stimulated lipolysis to the same extent as those used in Examples 1–3.

EXAMPLE 1

Lipolysis measurements on various plant extracts were conducted by using a method similar to that described by Chernick et al, J. of Lipid Research, (1986), 27, 266–294; Hirsch et al., J. of Lipid Research, (1984), 25, 665–677; Kawamura et al., Proc. Natl. Acd. Sci. USA, (1981), 78, 732–736. These methods were used to measure lipolytic activity of various agents.

Cell Culture

3T3-L1 mouse embryo fibroblasts (ATCC# CCL 92.1) were acquired from the American Type Culture Collection (Rockville, Md.) in a cryopreserved state and stored under liquid nitrogen until used. To initiate growth, the cells were rapidly thawed by shaking the cryo-ampule in a 37° C. bath, opening the ampule and pipetting the contents into a cell culture-treated (25 sq.cm.) T-flask containing 12 ml of media. The cells grew well in 90% Dulbecco's Modified Eagle's Medium (DMEM) containing 4.5 g/l D-glucose and L-glutamine with no sodium pyruvate (Gibco BRL, Cat #11965-068), 10% Fetal Bovine Serum, certified (Gibco BRL, Cat #16000) and 1% Antibiotic/Antimycotic liquid (100×) (Gibco BRL, Cat #15240-013). Cells were incubated at 37° C. in 5% $CO_2$, 95% air. In order to minimize variability by inadvertent selection through random subculturing, we performed a series of documented passages before using the cells in assays. This yielded a collection of flasks containing cells that were as identical in age and phenotype as possible. Each flask was trypsinized with 0.5% Trypsin-EDTA (Gibco BRL, Cat #15405-012). The cells were pelleted by centrifugation and then resuspended in 1 ml of a 1:1 mixture of 80% DMEM, 20% FBS and 85% DMEM, 15% DMSO in sterile cryogenic vials. The vials were immediately stored at −20° C. for 4 hours, then −70° C. overnight and then transferred to liquid nitrogen for long-term storage.

Cell Differentiation

For assay purposes one cryogenic vial was thawed and inoculated into 12 ml of media (see above) in a 25 sq. cm T-flask. The cells were allowed to divide until nearly confluent. At this point they were harvested from the flask with trypsin, pelleted by centrifugation, resuspended in media and equally dispensed into wells in two 12-well culture plates. The cells were then grown to confluence. Within 24 hours of achieving confluence (Day 0), the media was removed and fresh media containing 0.5 μM dexamethasone, 0.5 μM isobutyl-methyl-xanthine and 2 μM insulin was added to each well. On the second day after treatment with the lipogenic media, the media was aspirated and replaced with 2 ml per well of 90% DMEM, with low glucose (1000 mg/l), 10% FBS, 1% antibiotic/antimycotic (see above) and 0.1 μCi per ml. of [14 C]-U-glucose (ICN, Irvine, Calif., Cat. #11047, 250–360 mCi/mmol). After 7 days the media was aspirated and the cells were equilibrated in PBS with 3% FAFBSA for 15 minutes at 37° C. after which they were again aspirated and treated with 0.5 ml of PBS/3% FAFBSA containing the extract to be tested. Following a two hour incubation at 37° C. in air, the assay buffer was removed from each well and transferred to scintillation vials. After the addition of 10 ml of Scintiverse-BD scintillation cocktail, the total radioactivity in each sample was determined on a Beckman LS 5801 scintillation counter. The degree of stimulation elicited by the actives was calculated by dividing the average DPM in triplicate wells treated with actives by the average DPM in triplicate wells treated with PBS/3% FAFBSA only. The results are summarized in Table 1.

TABLE 1

LIPOLYSIS MEASUREMENT OF VARIOUS ACTIVES

| SUBSTANCE | % CONCENTRATION (WT./VOLUME) | FOLD INCREASE OVER CONTROL |
|---|---|---|
| CONTROL | | 1.0 |
| ISOPROTERENOL | 0.00002 | 3.4 |
| THEOPHYLLINE | 0.01 | 0.8 |
| | 0.05 | 1.9 |
| | 0.1 | 3.1 |
| CAFFEINE | 0.1 | 2.4 |
| YOHIMBINE | 0.002 | No Stimulation |
| GINKGO | 0.1 | 0.8 |
| BILOBA | 1.0 | 1.3 |
| POLYGALA | 0.01 | 0.9 |
| TENUIFOLIA | 0.05 | 4.3 |
| | 0.1 | 4.9 |
| PLATYCODON | 0.01 | 1.0 |
| GRAN. | 0.05 | 2.9 |
| | 0.1 | 4.2 |
| KOCHIA | 0.01 | 1.2 |
| SCOPARIA | 0.05 | 2.7 |
| | 0.1 | 4.2 |

As shown in Table 1, individual extracts of *Polygala tenuifolia*, *Platycodon grandiflorum* or *Kochia scoparia* as crude extracts showed a superior lipolytic effect over caffeine, or theophylline, or *Ginkgo biloba* at the same concentration. Although the extracts included in the invention were less active than isoproterenol, their use is preferred over isoproterenol—the latter is a drug with potentially undesirable side effects.

EXAMPLE 2

Lipolytic activities of various fractions (polar vs. nonpolar) of extracts were evaluated.

Fractionation of Extracts on Silica Gel

Extracts were dissolved in 0.1 ml EtOH/mg sample and sonicated if necessary for complete dissolution. They were then applied to silica gel columns (1 g silica gel/mg sample; prewashed with 3 ml/g silica gel EtOH and 5 ml/g silica EtOAc). The columns were eluted with, 1.4 ml EtOAc/g silica, 1 ml EtOH/g silica (EtOH 1), and 4 ml EtOH/g silica (EtOH 2), respectively. The fractions were concentrated to dryness under vacuum (max. temp. 40° C.). The resultant concentrates were redissolved in various solvents, as indicated in Table 2 and tested for lipolytic activity (described in Example 1).

The results that were obtained are summarized in Table 2.

TABLE 2

THE LIPOLYTIC ACTIVITY COMPARISON OF POLAR FRACTION VS. NON-POLAR FRACTION OF BOTANICALS

| SUBSTANCE | ELUENT | FOLD INCREASE OVER CONTROL |
|---|---|---|
| CONTROL | — | 1.0 |
| POLYGALA TEN. | Ethyl Acetate | 1.0 |
| | Ethanol 2 | 4.4 |
| PLATYCODON GRAN. | Ethyl Acetate | 1.4 |
| | Ethanol 2 | 3.7 |
| KOCHIA SCOP. | Ethyl Acetate | 3.6 |
| | Ethanol 2 | 3.8 |

As shown in Table 2, most of the lipolytic activity of *Polygala tenuifolia* and Platycodon was obtained from a polar fraction (ethanol).

EXAMPLE 3

Example 1 was repeated, except that various combinations of plant extracts within the scope of the invention were tested for lipolytic activity.

The results are summarized in Table 3.

TABLE 3

LIPOLYTIC ACTIVITIES OF PLANT EXTRACTS ALONE AND IN COMBINATION

| EXTRACT | CONCENTRATION (WT./VOLUME) | FOLD INCREASE OVER CONTROL |
|---|---|---|
| KOCHIA | 0.05% | 1.0 |
| | 0.1% | 1.3 |
| POLYGALA | 0.05% | 1.4 |
| | 0.1% | 2.6 |
| PLATYCODON | 0.05% | 2.9 |
| | 0.1% | 2.8 |
| KOCHIA + POLYGALA | each 0.05% | 2.3 |
| KOCHIA + PLATYCODON | each 0.05% | 2.6 |
| POLYGALA + PLATYCODON | each 0.05% | 2.6 |
| ALL THREE | each 0.05% | 2.6 |

EXAMPLE 4

Example 3 was repeated, except that lower concentrations of extracts were tested. The results are summarized in Table 4.

TABLE 4

LIPOLYTIC ACTIVITIES OF PLANT EXTRACTS ALONE AND IN COMBINATION

| EXTRACT | % CONCENTRATION (WT./VOLUME) | FOLD INCREASE OVER CONTROL |
|---|---|---|
| KOCHIA | 0.025 | 1.1 ± 0.03 |
| | 0.05 | 1.2 ± 0.08 |
| POLYGALA | 0.025 | 3.1 ± 0.4 |

TABLE 4-continued

LIPOLYTIC ACTIVITIES OF PLANT EXTRACTS
ALONE AND IN COMBINATION

| EXTRACT | % CONCENTRATION (WT./VOLUME) | FOLD INCREASE OVER CONTROL |
|---|---|---|
| | 0.05 | 3.2 ± 0.1 |
| PLATYCODON | 0.025 | 3.7 ± 0.2 |
| | 0.05 | 1.8 ± 0.2 |
| KOCHIA + POLYGALA | each 0.025 | 1.5 ± 0.1 |
| KOCHIA + PLATYCODON | each 0.025 | 1.9 ± 0.1 |
| POLYGALA + PLATYCODON | each 0.025 | 2.8 ± 0.2 |
| ALL THREE | each 0.025 | 2.2 ± 0.3 |

The results in Tables 3 and 4 demonstrate that the plant extracts within the scope of the invention exhibited lipolytic activity, when used alone, or in various combinations with each other.

EXAMPLE 5

This example illustrates a high internal phase water-in-oil emulsion in accordance with the invention:

| Fully hydrogenated coconut oil | 3.9% w/w |
|---|---|
| ceramide lipids | 0.1% |
| Sodium L-lactate | 2.0% |
| Oleth-2 | 5.0% |
| Quaternium-18-hectorite | 0.5% |
| *Polygala tenuifolia* ethanol extract | 0.5% |
| Caffeine | 3.0% |
| *Ginkgo biloba* extract (Phytelene) | 0.5% |
| Escin | 0.5% |
| preservative | 0.3% |
| MgSO4.7H2O | 0.3% |
| BHT | 0.01% |
| Perfume | qs |
| Water | to 100 |

EXAMPLE 6

This example illustrates an oil in water emulsion in accordance with the invention:

| volatile silicone | 10.0% |
|---|---|
| squalane | 15.0% |
| Petrolatum oil | 5.0% |
| lanolin | 4.0% |
| cetyl alcohol | 1.0% |
| stearic acid | 2.0% |
| Platycodon g. ethanol extract | 1.0% |
| Aminophylline | 0.5% |
| Glycerine | 5.0% |
| *Centella asiatica* extract (phytelene) | 0.3% |
| aloe vera | 0.5% |
| triethanol amine | 0.1% |
| preservative | 0.3% |
| Antioxidant | 0.01% |
| perfume | qs |
| Water | to 100 |

EXAMPLE 7

This example illustrates a hydroalcoholic gel in accordance with the invention:

| Carbopol 940 | 1.0% |
|---|---|
| Ethyl alcohol | 25.0% |
| Ivy extract (Alban Muller) | 0.5% |
| *Polygala tenuifolia* extract | 1.0% |
| Caffeine | 2.0% |
| Horsechestnut extract (Albert Muller) | 0.5% |
| *Ginkgo biloba* extract (phytelene) | 0.5% |
| Fruit acid (Albert Muller) | 2.0% |
| Silver birch extract (Botanicals International) | 0.5% |
| preservative | 0.05 |
| demineralized water | to 100 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method of reducing the signs of cellulite, the method comprising applying onto the skin, the composition comprising:

(a) from about 0.0001 to about 5%, by weight of the composition, of a plant extract selected from the group consisting of a polar extract of *Polygala tenuifolia*, an extract of *Platycodon grandiflorum*, an extract of *Kochia scoparia*, and mixtures thereof; and (b) a cosmetically acceptable vehicle.

2. The method of claim 1, the composition further comprising a xanthine.

* * * * *